United States Patent
Ellman et al.

(10) Patent No.: US 12,274,525 B2
(45) Date of Patent: Apr. 15, 2025

(54) SYSTEMS AND METHODS FOR TRACKING ANATOMICAL MOTION

(71) Applicant: Mazor Robotics Ltd., Caesarea (IL)

(72) Inventors: Aviv Ellman, Kfar Sava (IL); Moshe Shoham, Hoshaya (IL)

(73) Assignee: Mazor Robotics Ltd., Caesarea (IL)

( * ) Notice: Subject to any disclaimer, the term of this patent is extended or adjusted under 35 U.S.C. 154(b) by 792 days.

(21) Appl. No.: 17/464,300

(22) Filed: Sep. 1, 2021

(65) Prior Publication Data

US 2022/0096188 A1 Mar. 31, 2022

Related U.S. Application Data

(60) Provisional application No. 63/085,018, filed on Sep. 29, 2020.

(51) Int. Cl.
*A61B 34/20* (2016.01)
*A61B 34/00* (2016.01)
*A61B 34/10* (2016.01)
*A61B 34/30* (2016.01)

(52) U.S. Cl.
CPC .............. *A61B 34/77* (2016.02); *A61B 34/10* (2016.02); *A61B 34/20* (2016.02); *A61B 34/30* (2016.02); *A61B 2034/105* (2016.02); *A61B 2034/107* (2016.02); *A61B 2034/2059* (2016.02)

(58) Field of Classification Search
CPC ......... A61B 34/10; A61B 34/20; A61B 34/30; A61B 34/77; A61B 2017/00119; A61B 2017/00694; A61B 2034/105; A61B 2034/107; A61B 2034/2048; A61B 2034/2055; A61B 2034/2059;
(Continued)

(56) References Cited

U.S. PATENT DOCUMENTS

| | | |
|---|---|---|
| 5,329,933 A | 7/1994 | Graf |
| 6,152,890 A | 11/2000 | Kupfer et al. |
| 6,200,024 B1 | 3/2001 | Negralli |

(Continued)

FOREIGN PATENT DOCUMENTS

| | | |
|---|---|---|
| CA | 2958013 | 4/2017 |
| CN | 108186120 | 6/2018 |

(Continued)

OTHER PUBLICATIONS

Hennersperger et al., Towards MRI-Based Autonomous Robotic US Acquisitions: A First Feasibility Study, 2016, IEEE, p. 538-548 (Year: 2016).*

(Continued)

*Primary Examiner* — McDieunel Marc
(74) *Attorney, Agent, or Firm* — Sheridan Ross P.C.

(57) ABSTRACT

Methods and systems for detecting, monitoring, and accounting for anatomical motion is provided. An initial contact between a first robotic arm and an anatomical element of a patient is detected based on information received from at least one internal sensor of the first robotic arm. A position of the anatomical element is determined based on the information. The determined position is compared to an expected position of the anatomical element. A tool trajectory of a second robotic arm is updated when the determined position is offset from the expected position.

20 Claims, 4 Drawing Sheets

(58) Field of Classification Search
CPC ...... A61B 2034/2072; A61B 2090/064; A61B 2090/066
See application file for complete search history.

(56) References Cited

U.S. PATENT DOCUMENTS

| | | | |
|---|---|---|---|
| 6,435,715 | B1 | 8/2002 | Betz et al. |
| 6,582,121 | B2 | 6/2003 | Crain et al. |
| 6,644,852 | B2 | 11/2003 | Crain et al. |
| 7,198,630 | B2 * | 4/2007 | Lipow .................. A61B 34/76 606/1 |
| 7,567,834 | B2 * | 7/2009 | Clayton ................ A61B 5/06 600/427 |
| 7,708,741 | B1 * | 5/2010 | Bonutti ............. A61B 17/1666 606/88 |
| 7,899,226 | B2 | 3/2011 | Pescatore et al. |
| 7,907,166 | B2 | 3/2011 | Lamprecht et al. |
| 8,073,528 | B2 | 12/2011 | Zhao et al. |
| 8,108,072 | B2 | 1/2012 | Zhao et al. |
| 8,147,503 | B2 | 4/2012 | Zhao et al. |
| 8,392,022 | B2 | 3/2013 | Ortmaier et al. |
| 8,568,317 | B1 | 10/2013 | Gharib et al. |
| 8,611,495 | B2 | 12/2013 | Maschke |
| 8,721,566 | B2 | 5/2014 | Connor et al. |
| 8,781,630 | B2 | 7/2014 | Banks et al. |
| 8,870,889 | B2 | 10/2014 | Frey |
| 9,050,728 | B2 | 6/2015 | Ban et al. |
| 9,259,276 | B2 | 2/2016 | Mintz et al. |
| 9,259,278 | B2 | 2/2016 | Jensen |
| 9,259,282 | B2 | 2/2016 | Azizian et al. |
| 9,307,894 | B2 | 4/2016 | von Grunberg et al. |
| 9,402,689 | B2 | 8/2016 | Prisco et al. |
| 9,592,096 | B2 | 3/2017 | Maillet et al. |
| 9,649,072 | B2 | 5/2017 | Ragnarsdottir et al. |
| 9,662,174 | B2 | 5/2017 | Taylor et al. |
| 9,687,301 | B2 | 6/2017 | Lee et al. |
| 9,767,608 | B2 | 9/2017 | Lee et al. |
| 9,789,313 | B2 | 10/2017 | Lipani |
| 9,888,966 | B2 | 2/2018 | Farritor et al. |
| 9,895,813 | B2 | 2/2018 | Blumenkranz et al. |
| 9,969,090 | B2 | 5/2018 | Warashina et al. |
| 10,076,385 | B2 | 9/2018 | Shoham et al. |
| 10,149,729 | B2 | 12/2018 | Smaby et al. |
| 10,271,832 | B2 | 4/2019 | O'Neil et al. |
| 10,299,880 | B2 | 5/2019 | Ramirez Luna et al. |
| 10,368,054 | B2 | 7/2019 | Panescu et al. |
| 10,383,765 | B2 | 8/2019 | Alvarez et al. |
| 10,390,895 | B2 | 8/2019 | Henderson et al. |
| 10,456,076 | B2 | 10/2019 | Liu |
| 10,456,211 | B2 | 10/2019 | McAfee |
| 10,512,413 | B2 | 12/2019 | Schepis et al. |
| 10,561,384 | B2 | 2/2020 | Tanaka et al. |
| 10,668,625 | B2 | 6/2020 | Kuroda et al. |
| 10,675,098 | B2 | 6/2020 | Zhao et al. |
| 10,675,107 | B2 | 6/2020 | Steger et al. |
| 11,298,195 | B2 * | 4/2022 | Ye .......................... A61B 34/10 |
| 2004/0122427 | A1 | 6/2004 | Holmes |
| 2005/0096502 | A1 | 5/2005 | Khalili |
| 2006/0241414 | A1 | 10/2006 | Nowlin et al. |
| 2006/0258938 | A1 | 11/2006 | Hoffman et al. |
| 2007/0106307 | A1 | 5/2007 | Bodduluri et al. |
| 2007/0232958 | A1 | 10/2007 | Donofrio et al. |
| 2011/0069818 | A1 | 3/2011 | Muller |
| 2011/0087238 | A1 | 4/2011 | Wang et al. |
| 2011/0172566 | A1 | 7/2011 | Kawchuk |
| 2011/0172720 | A1 | 7/2011 | Metcalf, Jr. et al. |
| 2012/0029694 | A1 | 2/2012 | Mueller |
| 2012/0041562 | A1 | 2/2012 | Shachar et al. |
| 2013/0012831 | A1 | 1/2013 | Schmitz et al. |
| 2013/0096574 | A1 | 4/2013 | Kang et al. |
| 2013/0268007 | A1 | 10/2013 | Rezach et al. |
| 2014/0163736 | A1 | 6/2014 | Azizian et al. |
| 2014/0179997 | A1 | 6/2014 | von Grunberg et al. |
| 2014/0188132 | A1 | 7/2014 | Kang |
| 2014/0253684 | A1 | 9/2014 | Kumar et al. |
| 2014/0309659 | A1 | 10/2014 | Roh et al. |
| 2015/0297177 | A1 | 10/2015 | Boctor et al. |
| 2016/0081754 | A1 | 3/2016 | Kostrzewski et al. |
| 2016/0184032 | A1 | 6/2016 | Romo et al. |
| 2017/0273614 | A1 | 9/2017 | Giphart et al. |
| 2018/0064497 | A1 | 3/2018 | Hussain et al. |
| 2018/0193101 | A1 | 7/2018 | Hashimoto |
| 2018/0263530 | A1 | 9/2018 | Jung |
| 2018/0307314 | A1 | 10/2018 | Connor |
| 2018/0333061 | A1 | 11/2018 | Pracyk et al. |
| 2018/0368931 | A1 | 12/2018 | Hongo et al. |
| 2019/0069957 | A1 | 3/2019 | Barral et al. |
| 2019/0125460 | A1 | 5/2019 | Maillet et al. |
| 2019/0206565 | A1 | 7/2019 | Shelton, IV |
| 2019/0307519 | A1 | 10/2019 | Popovic |
| 2019/0357884 | A1 | 11/2019 | Williams et al. |
| 2019/0374299 | A1 | 12/2019 | Peine |
| 2020/0015806 | A1 | 1/2020 | Scheib et al. |
| 2020/0015923 | A1 | 1/2020 | Scheib et al. |
| 2020/0054215 | A1 | 2/2020 | Roche |
| 2020/0060775 | A1 | 2/2020 | Bonutti |
| 2020/0069377 | A1 | 3/2020 | Finley et al. |
| 2020/0113637 | A1 | 4/2020 | Ida et al. |
| 2020/0169673 | A1 | 5/2020 | King et al. |
| 2020/0179065 | A1 | 6/2020 | Crawford et al. |
| 2020/0205900 | A1 | 7/2020 | Buckland et al. |
| 2020/0261160 | A1 | 8/2020 | Peine et al. |
| 2020/0360099 | A1 | 11/2020 | Smaby et al. |
| 2021/0029307 | A1 | 1/2021 | King et al. |
| 2021/0298590 | A1 * | 9/2021 | Ayvali ............... A61B 1/00045 |
| 2021/0338348 | A1 | 11/2021 | Zahavi et al. |
| 2021/0402603 | A1 | 12/2021 | Murphy et al. |
| 2022/0160445 | A1 | 5/2022 | Meglan et al. |
| 2022/0241032 | A1 | 8/2022 | Zucker et al. |
| 2022/0395342 | A1 | 12/2022 | Weiss et al. |

FOREIGN PATENT DOCUMENTS

| | | |
|---|---|---|
| CN | 109171745 | 1/2019 |
| DE | 10042599 | 3/2002 |
| DE | 102012004506 | 9/2013 |
| DE | 102015217059 | 3/2017 |
| EP | 2289452 | 3/2011 |
| EP | 2757948 | 7/2014 |
| EP | 2467074 | 1/2019 |
| EP | 3492046 | 6/2019 |
| EP | 3492047 | 6/2019 |
| EP | 2739231 | 9/2019 |
| EP | 3551983 | 10/2019 |
| EP | 3060157 | 12/2019 |
| EP | 3609422 | 2/2020 |
| EP | 2879608 | 3/2020 |
| GB | 2156983 | 10/1985 |
| JP | 5207490 | 6/2013 |
| JP | 2019-524230 | 9/2019 |
| KR | 10-2019-114052 | 10/2019 |
| RO | 132416 | 3/2018 |
| WO | WO 95/01757 | 1/1995 |
| WO | WO 96/29930 | 10/1996 |
| WO | WO 00/35366 | 6/2000 |
| WO | WO 2007/025218 | 3/2007 |
| WO | WO 2007/038510 | 4/2007 |
| WO | WO 2010/068005 | 6/2010 |
| WO | WO 2011/149845 | 12/2011 |
| WO | WO 2012/168534 | 12/2012 |
| WO | WO 2014/106262 | 7/2014 |
| WO | WO 2017/002143 | 1/2017 |
| WO | WO 2018/203903 | 11/2018 |
| WO | WO 2019/036006 | 2/2019 |
| WO | WO 2019/206340 | 10/2019 |
| WO | WO 2020/072255 | 4/2020 |
| WO | WO 2020/079596 | 4/2020 |

(56) References Cited

FOREIGN PATENT DOCUMENTS

| WO | WO 2020/118244 | 6/2020 |
|---|---|---|
| WO | WO 2020/201353 | 10/2020 |

OTHER PUBLICATIONS

Vandini et al., Unified Tracking and Shape Estimation for Concentric Tube Robots, 2017, IEEE, p. 901-915 (Year: 2017).*
Haratian et al., Toward Flexibility in Sensor Placement for Motion Capture Systems: A Signal Processing Approach, 2013, IEEE, p. 701-709 (Year: 2013).*
Stolka et al., Improving Navigation Precision of Milling Operations in Surgical Robotics, 2007, IEEE, p. 2351-2357 (Year: 2007).*
International Preliminary Report on Patentability for International (PCT) Patent Application No. PCT/IB2021/058420, dated Apr. 13, 2023 10 pages.
Official Action with English Translation for Japan Patent Application No. 2021-514567, dated May 11, 2023, 12 pages.
Official Action with Machine Translation for China Patent Application No. 201980067844.9, dated Mar. 1, 2024, 27 pages.
Official Action for U.S. Appl. No. 17/344,658, dated Mar. 21, 2024 12 pages.
Official Action for U.S. Appl. No. 17/285,374, dated Feb. 6, 2024 16 pages.
Official Action for U.S. Appl. No. 17/285,374, dated May 8, 2024 15 pages.
Invitation to Pay Additional Fees for International (PCT) Patent Application No. PCT/IL2022/050126, dated May 27, 2022, 11 pages.
International Search Report and Written Opinion for International (PCT) Patent Application No. PCT/IL2022/050126, dated Jul. 18, 2022, 18 pages.
Extended Search Report for European Patent Application No. 19872498.1, dated Jun. 9, 2022, 9 pages.
Invitation to Pay Additional Fees for International (PCT) Patent Application No. PCT/IL2022/050603, dated Oct. 6, 2022, 13 pages.
International Search Report and Written Opinion for International (PCT) Patent Application No. PCT/IL2022/050603, dated Nov. 28, 2022, 21 pages.
Official Action with English Translation for Japan Patent Application No. 2021-514567, dated Sep. 26, 2023, 12 pages.
Official Action for U.S. Appl. No. 17/344,658, dated Aug. 4, 2023 6 pages Restriction Requirement.
Official Action for U.S. Appl. No. 17/344,658, dated Oct. 25, 2023 9 pages.
Official Action for U.S. Appl. No. 17/285,374, dated Aug. 30, 2023 14 pages.
Official Action for U.S. Appl. No. 17/575,404, dated Jun. 21, 2024 13 pages.
Official Action for U.S. Appl. No. 17/344,658, dated Jul. 15, 2024 10 pages.
Aranda-Valera et al. "Measuring Spinal Mobility Using an Inertial Measurement Unit System: A Validation Study in Axial Spondyloarthritis," Diagnostics, 2020, vol. 10, No. 6, Article 426, 13 pages.
Dai et al. "Vibration-Based Milling Condition Monitoring in Robot-Assisted Spine Surgery," IEEE/AMSE Transactions on Mechatronics, Dec. 2015, vol. 20, No. 6, pp. 3028-3039.
Leroy "Analysis of the spine through a multibody model and IMU technology," Ecole polytechnique de Louvain, Université catholique de Louvain, 2019, 90 pages [retrieved online Oct. 29, 2020 from: hdl.handle.net/2078.1/thesis:19491].
Voinea et al. "Measurement and Geometric Modelling of Human Spine Posture for Medical Rehabilitation Purposes Using a Wearable Monitoring System Based on Inertial Sensors," Sensors, 2017, vol. 17, No. 1, Article 3, 19 pages.

International Search Report and Written Opinion for International (PCT) Patent Application No. PCT/IL2022/050141, dated Jun. 8, 2022, 16 pages.
Official Action for U.S. Appl. No. 17/583,788, dated Aug. 19, 2024 6 pages Restriction Requirement.
International Search Report and Written Opinion for International (PCT) Patent Application No. PCT/IB2021/058420, dated Nov. 29, 2021 16 pages.
International Search Report and Written Opinion prepared by the Israel Patent Office on Dec. 31, 2019, for International Application No. PCT/IB2019/058795.
"Robotic Assisted Systems," Intuitive Surgical, Jul. 2019, 5 pages.
"Robot-Assisted Laparoscopic Procedures," EBESCO Information Services, Updated May 2014, 6 pages [retrieved online from: www.wkhs.com/cancer/cancer-treatment-services/surgery/robotic-surgery/robot-assisted-laparoscopic-procedures].
Abdelaal et al. "A multi-camera, multi-view system for training and skill assessment for robot- assisted surgery," International Journal of Computer Assisted Radiology and Surgery, May 2020, vol. 15, pp. 1369-1377.
Boctor et al. "A Dual-Armed Robotic System for Intraoperative Ultrasound Guided Hepatic Ablative Therapy: A Prospective Study," IEEE, Proceedings of the 2004 IEEE International Conference on Robotics & Automation, New Orleans, LA, Apr. 2004, pp. 2517-2522.
Cao et al. "A Novel Robotic Suturing System for Flexible Endoscopic Surgery," IEEE, 2019 International Conference on Robotics and Automation (ICRA), May 20-24, 2019, Montreal, Canada, 7 pages.
He et al. "A Multi-Function Force Sensing Instrument for Variable Admittance Robot Control in Retinal Microsurgery," 2014 IEEE International Conference on Robotics and Automation (ICRA), 2014, pp. 1411-1418.
Joskowicz "Computer-aided surgery meets predictive, preventive, and personalized medicine," EPMA Journal, 2017, vol. 8, 4 pages.
Khandalavala "Emerging surgical robotic technology: a progression toward microbots," Annals of Laparoscopic and Endoscopic Surgery, Jan. 2020, vol. 5, Article 3, 18 pages.
Kim et al. "Robot-Assisted Cardiac Surgery Using the Da Vinci Surgical System: A Single Center Experience," Korean Journal of Thoracic and Cardiovascular Surgery, 2015, vol. 48, pp. 99-104.
Kong et al. "Da Vinci Tool Torque Mapping over 50,000 Grasps and its Implications on Grip Force Estimation Accuracy," 2018 International Symposium on Medical Robotics (ISMR), 2018, 6 pages.
Kumar et al. "Emerging role of robotics in urology," Journal of Minimal Access Surgery, Oct. 2005, vol. 1, No. 4, pp. 202-210.
Li et al. "Design of a Multi-Arm Surgical Robotic System for Dexterous Manipulation," Journal of Mechanisms and Robotics, Dec. 2016, vol. 8, article 061017, 10 pages.
Matthews "How better data, 5G, and surgical robots will improve healthcare," The Robot Report, Sep. 29, 2019, 12 pages [retrieved online from: www.therobotreport.com/better-data-advancing-healthcare-robotics].
Seibold "An Advanced Force Feedback Tool Design for Minimally Invasive Robotic Surgery," Technische Universität München, May 15, 2012, Doctoral Engineers dissertation, 218 pages.
Staub "Micro Endoscope based Fine Manipulation in Robotic Surgery," Technische Universitat Munchen Lehrstuhl Robotic und Echtzeitsysteme, Dissertation, Apr. 2013, 146 pages.
Tian et al. "A Robot-Assisted Surgical System Using a Force-Image Control Method for Pedicle Screw Insertion," PLOS One, Jan. 2014, vol. 9, No. 1, article e86346, 9 pages.
Valeo "Scarless Surgery: The benefits and drawbacks of robotic thryroidectomy," ENTtoday, Apr. 1, 2010, 4 pages [retrieved online from: www.enttoday.org/article/scarless-surgery-the-benefits-and-drawbacks-of-robotic-thryroidectomy/].
Vivek et al. "Study of Neuroarm and Force Sensing Grippers in Robo-Assisted Neurosurgery," International Journal of Current Engineering and Technology, Mar. 2016, Special Issue 4, pp. 444-447.

* cited by examiner

FIG. 4

SYSTEMS AND METHODS FOR TRACKING ANATOMICAL MOTION

CROSS REFERENCE TO RELATED APPLICATIONS

This application claims the benefit of U.S. Provisional Application No. 63/085,018, filed on Sep. 29, 2020, and entitled "Systems and Methods for Tracking Anatomical Motion", which application is incorporated herein by reference in its entirety.

FIELD

The present technology is related generally to monitoring anatomical motion, and more particularly, to detecting and tracking anatomical motion via one or more internal sensor of a robotic arm.

BACKGROUND

Surgical procedures using robotic systems rely on a navigation system to track positions of various components and elements of the surgical procedures, such as tools, robotic arms, and patient anatomy. These positions may be identified and tracked by reference markers tracked by the navigation system. Components or elements that are unable to receive a reference marker may not be tracked by the navigation system and may not be tracked or may be tracked by other means.

SUMMARY

Example aspects of the present disclosure include:

A method of tracking anatomical motion according to at least one embodiment of the present disclosure comprises detecting, based on information received from at least one internal sensor of a first robotic arm, an initial contact between the first robotic arm and an anatomical element of a patient; determining, based on the information, a position of the anatomical element; comparing the determined position of the anatomical element to an expected position of the anatomical element; and when the determined position is offset from the expected position, updating a tool trajectory of a second robotic arm based on the comparison.

Any of the aspects herein, further comprising: registering the first robotic arm and the second robotic arm to a patient space corresponding to the patient.

Any of the aspects herein, wherein the expected position is based on a surgical plan.

Any of the aspects herein, further comprising: calculating a compensation parameter based on the comparison; wherein updating the tool trajectory of the second robotic arm based on the comparison comprises applying the compensation parameter to the tool trajectory.

Any of the aspects herein, wherein the at least one internal sensor comprises a force sensor and a torque sensor.

Any of the aspects herein, wherein the at least one internal sensor comprises an encoder.

Any of the aspects herein, further comprising: causing the first robotic arm to be secured to the anatomical element; and activating the first robotic arm to move the anatomical element to the expected position.

Any of the aspects herein, further comprising: causing the first robotic arm to be secured to the anatomical element; detecting, based on data received from the at least one internal sensor, movement of the first robotic arm; and determining, based on the detected movement, a movement of the anatomical element.

Any of the aspects herein, further comprising: updating a virtual model of an anatomical portion of the patient based on the determined movement of the anatomical element.

Any of the aspects herein, further comprising: causing the second robotic arm to move based on the determined movement of the anatomical element.

Any of the aspects herein, further comprising: causing the first robotic arm to be secured to the anatomical element; and activating the first robotic arm to prevent movement of the anatomical element from the determined position.

Any of the aspects herein, wherein the information is first information, the method further comprising: receiving second information from at least one second internal sensor of the second robotic arm, the second information corresponding to at least one of an applied force or an applied torque exerted by the second robotic arm on the anatomical element; and causing the first robotic arm to exert at least one of a responsive force or a responsive torque on the anatomical element to counteract the applied force or the applied torque.

A method of controlling a robotic arm according to at least one embodiment of the present disclosure comprises registering a first robotic arm and a second robotic arm to a patient space corresponding to a patient; receiving a surgical plan comprising information about an anatomical element of the patient and a surgical task to be completed on the anatomical element by the second robotic arm; causing the first robotic arm to grip the anatomical element with a mechanical gripper; and detecting, based on sensor data received from at least one internal sensor of the first robotic arm and without use of data from any external sensor, at least one force or torque exerted on the anatomical element by the second robotic arm.

Any of the aspects herein, further comprising: comparing the detected at least one force or torque to a corresponding predicted at least one force or torque described in the surgical plan; and generating an alert when the detected at least one force or torque differs from the predicted at least one force or torque by more than a predetermined amount.

Any of the aspects herein, further comprising: detecting an initial contact between the first robotic arm and the anatomical element, based on information from the at least one internal sensor; calculating a position of the anatomical element based on a position of the first robotic arm at a time of the detected initial contact; and comparing the calculated position of the anatomical element to a predicted position of the anatomical element from the surgical plan.

Any of the aspects herein, further comprising: generating a compensation parameter based on the comparison; and causing the second robotic arm to move based at least in part on the compensation parameter.

Any of the aspects herein, wherein the anatomical element is a vertebra.

A system for accounting for anatomical movement during a surgical procedure according to at least one embodiment of the present disclosure comprises a working robotic arm; a detecting robotic arm comprising at least one internal sensor configured to detect at least one of a force or a torque exerted on the working robotic arm; at least one processor; and at least one memory storing instructions for execution by the at least one processor that, when executed, cause the at least one processor to: receive a surgical plan comprising information about an anatomical element of a patient and a surgical task to be completed on the anatomical element by the working robotic arm; correlate a position of the detecting robotic arm to a position of the anatomical element; detect, based solely on sensor data received from at least one internal sensor, a movement of the detecting robotic arm resulting from a movement of the anatomical element during execution of the surgical task; and control movement of the detecting robotic arm during execution of the surgical task based on the detected movement.

Any of the aspects herein, wherein the at least one internal sensor comprises an encoder configured to sense at least one of an applied force or an applied torque.

Any of the aspects herein, wherein the surgical plan comprises information about a predicted force or torque to be exerted on the anatomical element by the working robotic arm during execution of the surgical task, and the at least one memory stores additional instructions for execution by the at least one processor that, when executed, cause the at least one processor to: detect, based solely on information received from the at least one internal sensor, a force or a torque exerted on the anatomical element by the working robotic arm; and compare the detected force or torque to the predicted force or torque.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

When conducting a robotically executed task or procedure (e.g., pilot hole drilling, bone removal, screw insertion, implant insertion, etc.) on a spinal segment or other anatomical element, forces and torques are exerted on the anatomic element, which may generate undesired motion of the anatomical element. Such undesired motion may cause inaccuracies in the executed procedure. For example, robotically guided accessories that directly contact the anatomical element may suffer from potential skiving. Skiving is the undesired slip of a tool relative to a cortical bone surface due to a steep contact angle between the tool and the cortical surface.

The use of two robotic arms can help detect this type of behavior, generate an alert, and/or mitigate it. When using two robotic arms, one arm is used to rigidly hold the anatomical element, such as a vertebra for example, in position, whether directly by a gripper or by gripping a custom hardware rigidly anchored to the anatomical element, while the other robotic arm executes the procedure. The first arm holding the anatomical element may also have an integrated sensing mechanism that enables the sensing of forces and torques channeled to it through the rigidly gripped anatomical element. This allows for continuous monitoring and alerting when undesired forces/torques are detected on the anatomical element. Moreover, the second arm can predict a relative motion vector and compensate for it until forces/torque values are acceptable. This collaboration of the two robotic arms results in minimizing the relative motion, which results in executing the plan with high accuracy.

Embodiments of the present disclosure comprise determining a position of an anatomical element based on a first robotic arm contacting, being secured to, or otherwise being correlated to the anatomical element. A movement of or a position of the first robotic arm (and thus, the anatomical element) may be determined or detected based on sensor data received from an internal sensor of the first robotic arm. In other embodiments, a force or torque exerted on the anatomical element by a second robotic arm may be detected based on the internal sensor of the first robotic arm. Such force or torque may correlate to movement of the anatomical element. In any way movement of the anatomical element is determined, several responses may occur based on such determined movement. For example, a tool trajectory of the second robotic arm may be adjusted, the first robotic arm may apply a reactive or compensative force, and/or the first robotic arm may move the anatomical element back to its initial position.

As described more fully below, methods and systems for tracking anatomical movement according to at least some embodiments of the present disclosure may beneficially utilize a robotic system operating in a single coordinate system with multiple arms, using integrated sensors with high accuracy. Such integrated sensors may provide accurate information or sensor data concerning the anatomical element, based on forces or torques measured in the robotic arm. The methods and systems may also provide a robotic system that increases accuracy of surgical procedures or otherwise alerts a surgeon or operator of movement of the anatomical element, thereby reducing and preventing unnecessary damage to patient anatomy.

Figure 1:
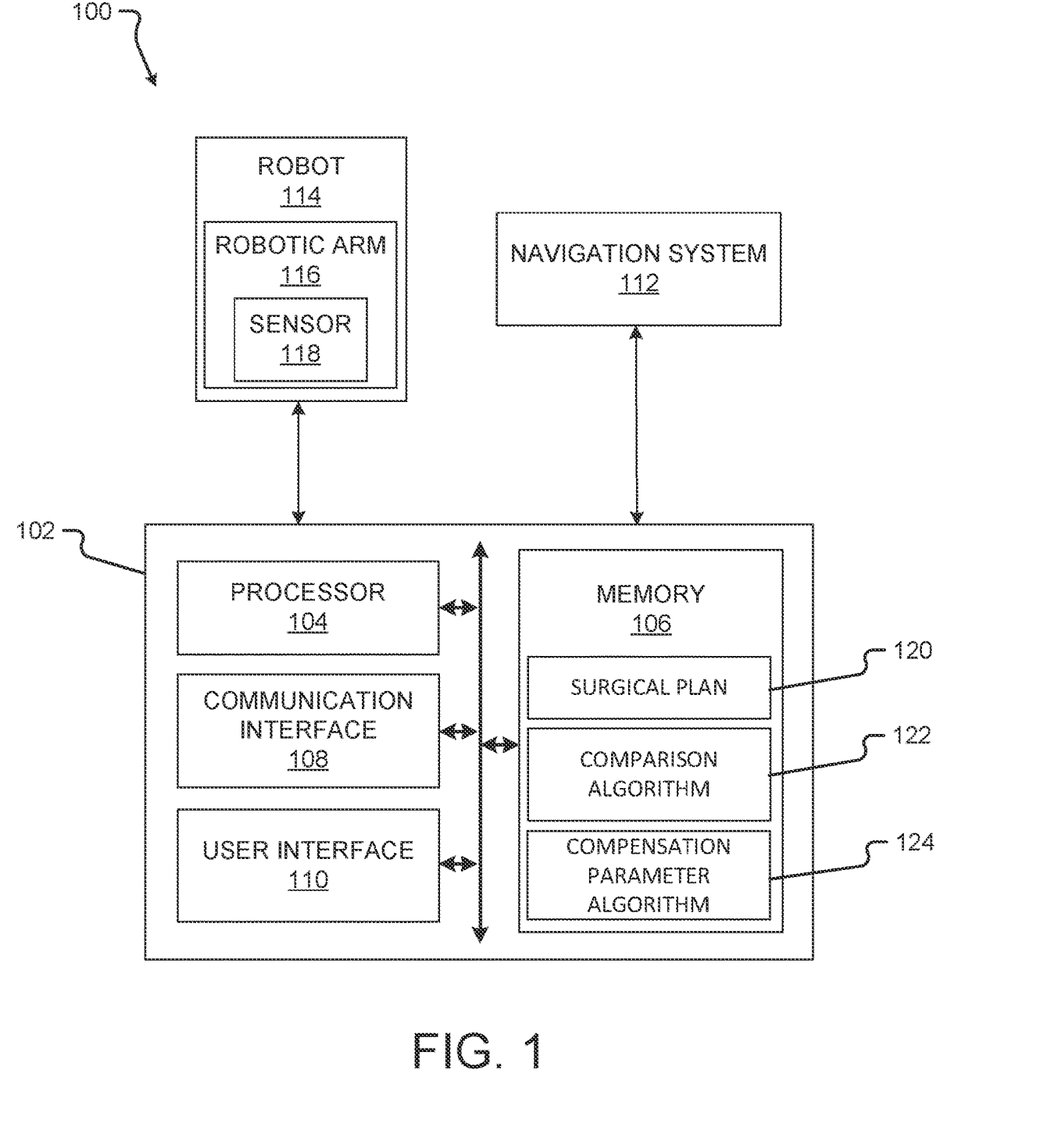
FIG. 1 is a block diagram of a system according to at least one embodiment of the present disclosure.

Turning first to FIG. 1, a block diagram of a system 100 according to at least one embodiment of the present disclosure is shown. The system 100 may be used to execute a comparison algorithm 122 and/or a compensation parameter algorithm 124 and/or to carry out other aspects of one or more of the methods disclosed herein. The system 100 comprises a computing device 102, a navigation system 112, a robot 114 having a robotic arm 116, and/or a sensor 118. Systems according to other embodiments of the present disclosure may comprise more or fewer components than the system 100. For example, the system 100 may not include the navigation system 112.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the navigation system 112, the robot 114, and/or the sensor 118.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300 and/or 400 described herein. The memory 106 may store, for example, one or more surgical plans 120, one or more comparison algorithms 122, and/or one or more compensation parameter algorithms 124. Such algorithms may, in some embodiments, be organized into one or more applications, modules, packages, layers, or engines. The algorithms may cause the processor 104 to manipulate data stored in the memory 106 and/or received from the navigation system 112, the robot 114, and/or the sensor 118.

The computing device 102 may also comprise a communication interface 108. The communication interface 108 may be used for receiving information from an external source (such as the navigation system 112, the robot 114, and/or the sensor 118), and/or for transmitting instructions, images, or other information to an external system or device (e.g., another computing device 102, the navigation system 112, the robot 114, and/or the sensor 118). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. In some embodiments, the user interface 110 may receive information and/or commands from a user via voice activation. In other embodiments, the user interface 110 may incorporate augmented reality or virtual reality. The user interface 110 may be used, for example, to receive a user selection or other user input regarding detecting an initial contact between a first robotic arm and an anatomical element of a patient; to receive a user selection or other user input regarding determining a position of the anatomical element; to receive a user selection or other user input regarding comparing the determined position to an expected position; to receive a user selection or other user input regarding updating a tool trajectory of a second robotic arm when the determined position is offset from the expected position; to receive a user selection or other user input regarding registering a first robotic arm and a second robotic arm to a patient space; to receive a user selection or other user input regarding receiving a surgical plan such as the surgical plan 120; to receive a user selection or other user input regarding correlating a position of a detecting robotic arm to a position of the anatomical element; to receive a user selection or other user input regarding causing the first robotic arm to grip an anatomical element; to receive a user selection or other user input regarding controlling movement of the detecting robotic arm during execution of the surgical task based on the detected movement; and/or to receive a user selection or other user input regarding detecting at least one force or torque exerted on the anatomical element by the second robotic arm. In some embodiments, the user interface 110 may be useful to allow a surgeon or other user to modify the plan 120, or other information displayed, though it will be appreciated that each of the preceding inputs may be generated automatically by the system 100 (e.g., by the processor 104 or another component of the system 100) or received by the system 100 from a source external to the system 100. In some embodiments, user input such as that described above may be optional or not needed for operation of the systems, devices, and methods described herein.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remote from one or more other components of the computer device 102.

The navigation system 112 may provide navigation for a surgeon and/or a surgical robot during an operation. The navigation system 112 may be any now-known or future-developed navigation system, including, for example, the Medtronic StealthStation™ S8 surgical navigation system. The navigation system 112 may include a camera or other sensor(s) for tracking one or more reference markers, navigated trackers, or other objects within the operating room or other room where a surgery takes place. In various embodiments, the navigation system 112 may be used to track a position of the robot 114 (or, more particularly, of a navigated reference marker attached, directly or indirectly, in fixed relation to the robot 114). The navigation system 112 may include a display for displaying one or more images from an external source (e.g., the computing device 102 or other source) or a video stream from the camera or other sensor of the navigation system 112.

In some embodiments, the navigation system 112 may be used to track movement of the robot 114 and may provide feedback regarding or confirmation of a position of the robot 114 or of the robotic arm 116. In such embodiments, the navigation system 112 may track the robot 114 and/or the robotic arm 116 by detecting a navigated tracking marker affixed thereto. The navigation system 112 may indicate, for example—audibly and/or visually via a display—that the robot 114 or the robotic arm 116 needs to be moved, automatically or manually, to a suggested robot pose. The navigation system 112 can monitor or track the robot 114 or the robotic arm 116 as the robot 114 or the robotic arm 116 is moved toward the suggested robot pose. The navigation system 112 can further indicate to or alert a user when the robot 114 or the robotic arm 116 has reached the suggested robot pose. In other embodiments, a user may view a display of the navigation system 112 while moving the robot 114 or the robotic arm 116 to the suggested robot pose, so as to ensure that the user moves the robot 114 or the robotic arm 116 to the correct pose. In some embodiments, the system 100 can operate without the use of navigation system 112.

The robot 114 may be any surgical robot or surgical robotic system. The robot 114 may be or comprise, for example, the Mazor X™ Stealth Edition robotic guidance system. The robot 114 may comprise one or more robotic arms 116. In some embodiments, the robotic arm 116 may comprise a plurality of robotic arms, though the robot 114 may comprise one robotic arm, two robotic arms, or more than two robotic arms. The robotic arm 116 may be used to selectively hold any tool or instrument and/or to be secured to an anatomical element of a patient. In some embodiments, the robotic arm 116 has at least five degrees of freedom. In other embodiments, the robotic arm 116 has at least six degrees of freedom. In yet other embodiments, the robotic arm 116 has fewer than five or greater than six degrees of freedom. The robotic arm 116 (and/or a base of the robot 114, shown in FIG. 2) may also have three dimensions of orientation. The combination of multiple degrees of freedom and multiple dimensions of orientation allows for the robotic arm 116 to move to any pose. In other words, the robotic arm 116 is not limited to a fixed area and can move in any direction. Further, in some embodiments, the robot 114 can move during a surgical procedure to position the robotic arm 116 (and thus, a tool or instrument) within reach of a desired or predetermined pose.

Reference markers (e.g., navigation markers) may be placed on the robot 114, the robotic arm 116, and/or any other object in the surgical space. The reference markers may be tracked by the navigation system 112, and the results of the tracking may be used by the robot 114 and/or by an operator of the system 100 or any component thereof. As described above, in some embodiments, the navigation system 112 can be used to track any other components of the system 100.

The robot 114 comprises one or more sensors 118 operable to measure or monitor a characteristic of the robot 114 or the robotic arm 116. The characteristic may include, but is not limited to, a force or torque experienced by the robotic arm 116 and/or the robot 114, and/or a position of the robot 114 and/or the robotic arm 116. Each sensor 118 may be any kind of sensor 118 for measuring the characteristic herein. The sensor 118 may include one or more or any combination of components that are electrical, mechanical, electro-mechanical, magnetic, electromagnetic, or the like. The sensor 118 may include, but is not limited to, one or more of a torque sensor, a force sensor, a linear encoder, a rotary encoder, a capacitor, and/or an accelerometer. In some embodiments, the sensor 118 may include a memory for storing sensor data. In still other examples, the sensor 118 may output signals (e.g., sensor data) to one or more sources (e.g., the computing device 102, the navigation system 112, and/or the robot 114).

The sensor 118 may be integrated internally into the robotic arm 116 or otherwise positioned inside of the robotic arm. In some embodiments, the sensor 118 is positioned inside a joint (shown in FIG. 2) of the robotic arm 116. The sensor 118 may include a plurality of sensors and each sensor may be positioned at the same location or a different location as any other sensor. For example, a sensor 118 may be positioned in one or more joints of the robotic arm 116. It will be appreciated that in some embodiments the sensor(s) 118 can be positioned at or on any component of the system 100 or environment (e.g., on any portion of the navigation system 112, the robot 114, the robotic arm 116, and/or any other component at the surgical site).

The sensor 118 may be operable to sense and/or monitor a force exerted on an anatomical element by the robotic arm 116 and/or to sense movement of the robotic arm 116 and/or the anatomical element (via the robotic arm 116). Data regarding the measured or monitored characteristic may be directly useful (e.g., a measured force may be compared to an expected force) and/or indirectly useful (e.g., a sudden increase in force may indicate that the anatomical element has moved). The sensor 118 may send the data to the computing device 102 when the sensor 118 detects a change in the characteristic. Further, in some embodiments, the sensor 118 may send data to the computing device 102 to display on the user interface 110 or otherwise notify the surgeon or operator of the change in the characteristic. In other embodiments, the sensor 118 may alert the surgeon or operator of the change in the characteristic by an alert such as, but not limited to, a sound or a light display. The sensor 118 may advantageously provide a safety function by monitoring and alerting the surgeon or operator of the force meeting or exceeding a predetermined threshold, thereby alerting the surgeon or operator of potential issues with the robot 114 and/or the robotic arm 116.

In some examples, the sensor 118 may trigger the computing device 102 to determine a position of an anatomical element based on the sensor data, compare the determined position with an expected position of the anatomical element, and update a tool trajectory of the robotic arm 116 based on the comparison when the determined position is offset from the expected position. The sensor 118 may also trigger the computing device 102 to calculate a compensation parameter based on the comparison and update the tool trajectory of the robotic arm 116 by applying the compensation parameter to the tool trajectory. The sensor 118 may further trigger the computing device 102 to cause the robotic arm 116 to exert at least one of a responsive force or a responsive torque on the anatomical element to counteract an applied force or applied torque on the anatomical element sensed by the sensor 118.

Figure 2:
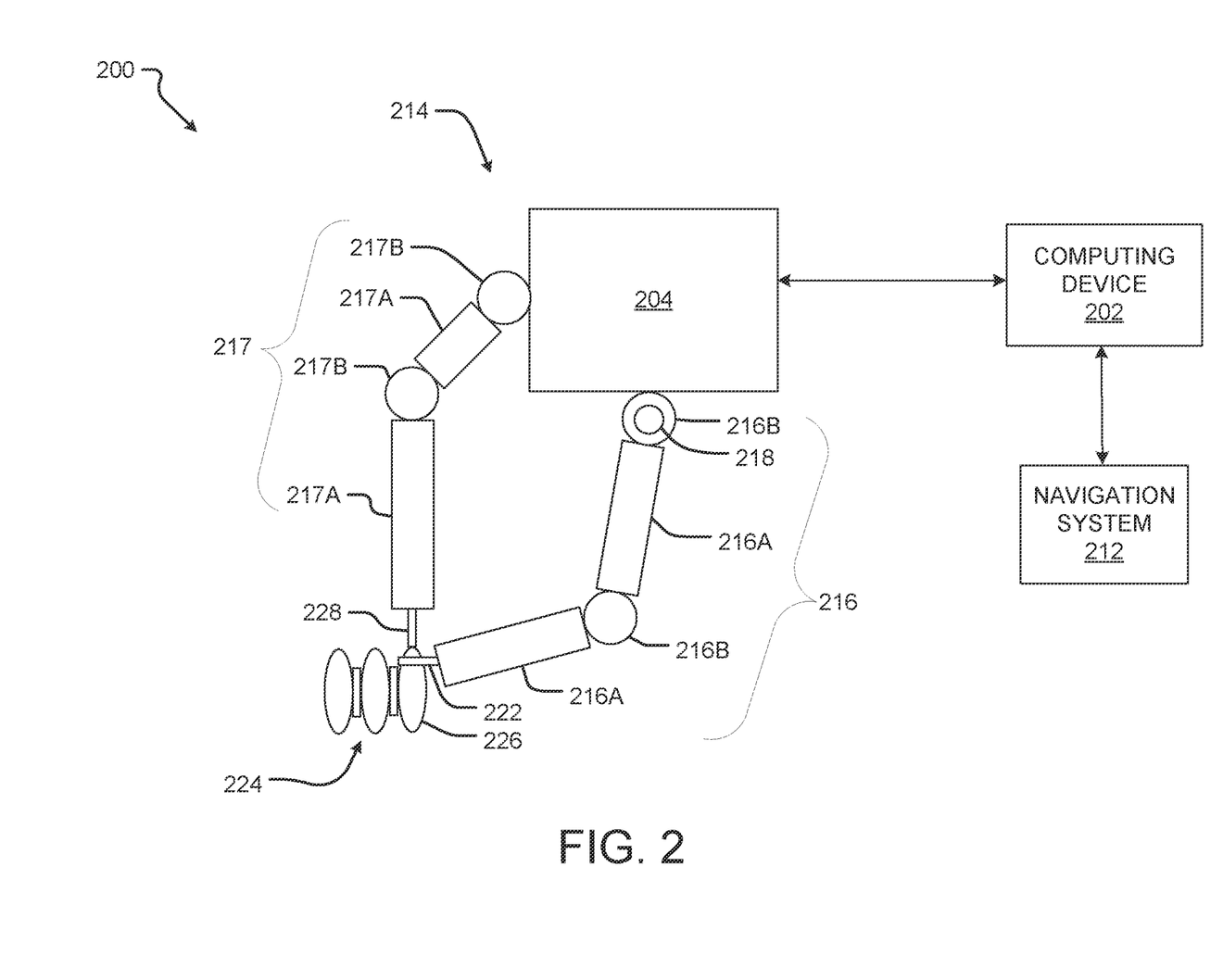
FIG. 2 is a diagram of a system according to at least one embodiment of the present disclosure.

Turning to FIG. 2, a block diagram of another system 200 according to at least one embodiment of the present disclosure is shown. The system 200 includes a computing device 202 (which may be the same as or similar to the computing device 102 described above), a navigation system 212 (which may be the same as or similar to the navigation system 112 described above), and a robot 214 (which may be the same as or similar to the robot 214 described above). Systems according to other embodiments of the present disclosure may comprise more or fewer components than the system 200. For example, the system 200 may not include the navigation system 212.

As illustrated, the robot 214 includes a first or detecting robotic arm 216 (which may comprise one or more members 216A connected by one or more joints 216B) and a second or a working robotic arm 217 (which may comprise one or more members 217A connected by one or more joints 217B), each extending from a base 204. In other embodiments, the robot 214 may include one robotic arm or two or more robotic arms. The base 204 may be stationary or movable. One or more tools or instruments may be disposed on an end of each of the first or detecting robotic arm 216 and the second or working robotic arm 217, though the tools or instruments may be disposed on any portion of the first or detecting robotic arm 216 and/or the second or working robotic arm 217. The first or detecting robotic arm 216 and/or the second or working robotic arm 217 is operable to execute one or more planned movements and/or procedures autonomously and/or based on input from a surgeon or operator.

In at least one embodiment, the first or detecting robotic arm 216 is secured to an anatomical element 226. In the illustrated embodiment, the anatomical element 226 is a vertebra of a spinal region 224. The first or detecting robotic arm 216 may be secured to the anatomical element 226 in any form. In the illustrated embodiment, the first or detecting robotic arm 216 is secured to the anatomical element 226 via a gripper 222. In other embodiments, the first or detecting robotic arm 216 may be attached to the anatomical element 226 with one or more screws, clamped to the anatomical element 226, or otherwise secured to the anatomical element 226, whether using one or more mechanical fasteners, a chemical adhesive, or otherwise. While the first or detecting robotic arm 216 is secured to the anatomical element 226, the second or working robotic arm 217 may have a tool or instrument 228 disposed at an end of the second or working robotic arm 217. The tool 228 may be used by the second or working robotic arm 217 to perform a procedure on the anatomical element 226, whether based on instructions from a surgeon and/or pursuant to a surgical plan. While the second or working robotic arm 217 uses the tool 228 to perform the procedure, movement of the anatomical element 226 may be monitored and undesired movement may be detected from an integrated sensor 218 of the first or detecting robotic arm 216.

The sensor 218 (which may be the same as or similar to the sensor 118 described above, and of which more than one may be included in the robotic arm 216 and/or 217) may be integrated into a joint 216B of the first or detecting robotic arm 216. Though the sensor 218 is shown integrated into the joint 216B nearest the base 204, the sensor 218 may be integrated into any joint 216B, 217B, any member 216A, 217A, or any portion of the first or detecting robotic arm 216, the second or working robotic arm 217, and/or the robot 214. Furthermore, more than one sensor 218 may be integrated into the first or detecting robotic arm 216, the second or working robotic arm 217, and/or the robot 214. As similarly described above, the sensor 218 may be one or more of a torque sensor, a force sensor, or an encoder integrated into the joint 216B. The sensor 218 is configured to sense at least one of an applied force or an applied torque exerted on the first or detecting robotic arm 216. As a result, the sensor 218 may detect a force or torque exerted by the second or working robotic arm 217 on the anatomical element 226 to which the first or working robotic arm 216 is secured. As will be described below with respect to FIGS. 3 and 4, such sensor data may be used to determine movement of the anatomical element 226.

In some embodiments, where the second or working robotic arm 217 performs a procedure (e.g., a surgical procedure such as, for example, drilling), sensor data from the sensor 218 of the first or detecting robotic arm 216 may be provided to, for example, the processor 104 for processing. Because the first or detecting robotic arm 216 does not perform the procedure, the first or detecting robotic arm 216 may be positioned and/or oriented in an optimized pose for obtaining sensor data. Further, in some instances, the first or detecting robotic arm 216 may be stationary and/or may not be receiving or exerting any forces, thereby enabling the first or detecting robotic arm 216 to obtain sensor data without obstructions.

Figure 3:
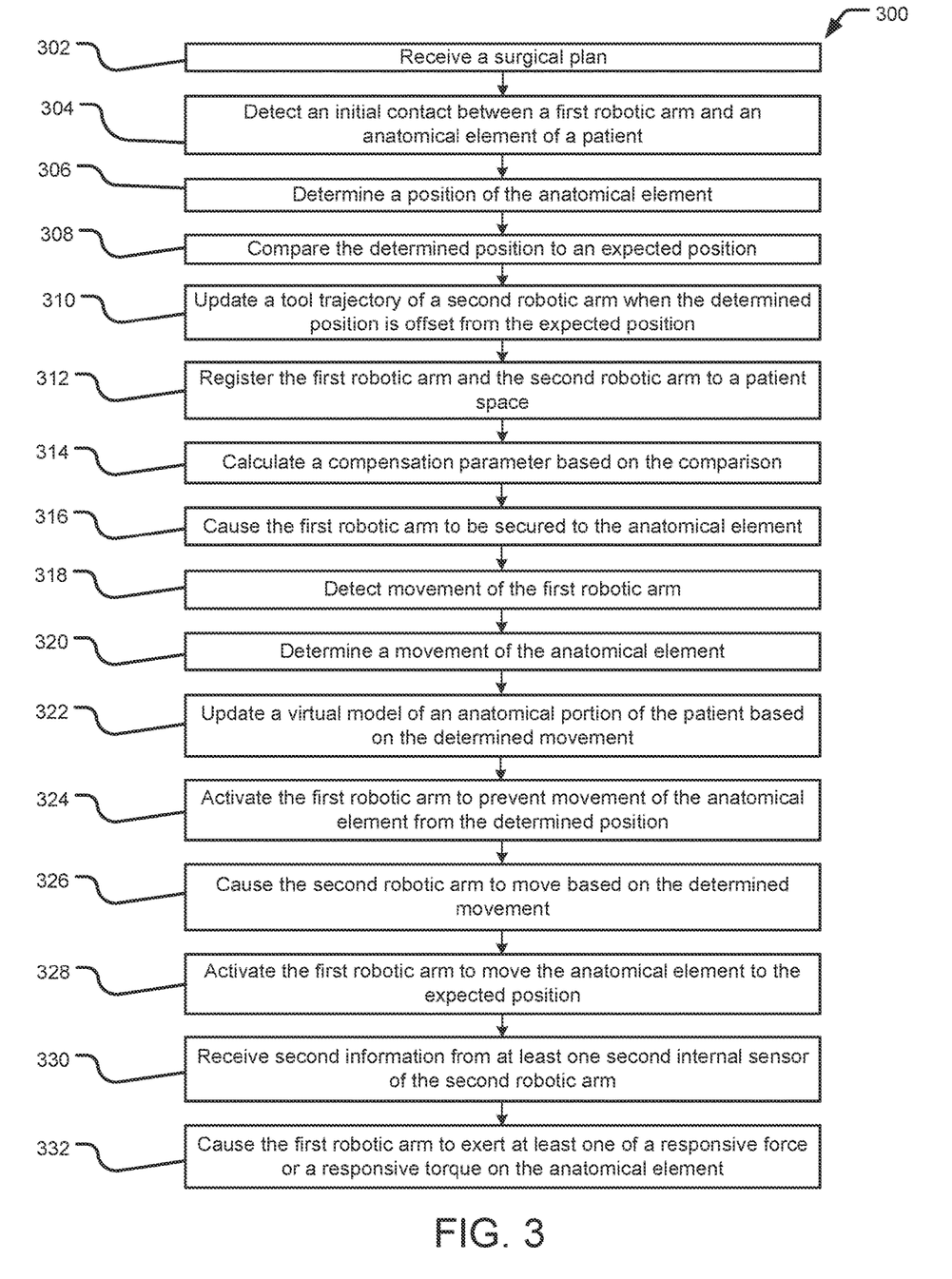
FIG. 3 is a flowchart of a method according to at least one embodiment of the present disclosure.

Turning now to FIG. 3, a method 300 for tracking anatomical motion may be executed in whole or in part, for example, on a computing device such as the computing device 102 or 202 or similar device, and may utilize one or more other components of the system 100 or 200 or similar components. One or more aspects of the method 300 may be performed by or with a robot such as the robot 114 or 214, a surgeon, or a combination of a surgeon and a robot.

The method 300 comprises receiving a surgical plan such as the surgical plan 120 (step 302). The surgical plan may be received via a user interface (e.g., the user interface 110) and/or a communication interface (e.g., the communication interface 108) of a computing device such as the computing device 102 or 202, and may be stored in a memory such as the memory 106 of the computing device. The surgical plan may include information about an anatomical element, such as the anatomical element 226, of the patient and/or about a surgical task to be completed on the anatomical element. The anatomical element may be a vertebra in some embodiments. The information may include information about a position and/or orientation of the anatomical element. The information may also include information about a first robotic arm, such as the robotic arm 116 or the first robotic arm 216, and/or a second robotic arm, such as the robotic arm 116 or the second robotic arm 217, that may perform the surgical task. The surgical plan may also include information about one or more planned movements of the second robotic arm. In some embodiments, the surgical plan includes a planned trajectory or path of the second robotic arm. The information may also include an expected position of the anatomical element (e.g., a position and/or orientation of the anatomical element). The information may further include a predicted force or torque that may be experienced by the anatomical element from the second robotic arm.

The method 300 comprises detecting an initial contact between the first robotic arm and the anatomical element of a patient (step 304). The detecting may be based on information received from at least one internal sensor such as the sensor 118 or 218 of the first robotic arm. The information may be received by the computing device, and more particularly, by a processor such as the processor 104 of the computing device. The information may be or comprise raw sensor data received directly from the internal sensor, or the information may be or comprise processed sensor data. In other embodiments, the information may be received via the user interface and/or via the communication interface of the computing device, and may be stored in the memory. In some embodiments, the information may be indirectly received via any other component of the system or a node of a network to which the system is connected. The sensor data or information may include force data, torque data, or positional data of the first robotic arm and/or the second robotic arm. Such information, as described below, may be useful for determining a position and/or movement of the anatomical element.

The method 300 also comprises determining a position of the anatomical element (step 306). The determining may be based on the information received from at least one internal sensor such as the sensor 118 or 218 of the first robotic arm. Such information or other sensor data may be used to determine a position of the first robotic arm (e.g., as detected at the moment of initial contact between the first robotic arm and the anatomical element). The determined position of the first robotic arm may then be used to determine a position of the anatomical element (e.g., based on one or more of a known position of the first robotic arm, known dimensions of the first robotic arm, and/or known dimensions of the anatomical element). In some embodiments, information (obtained from one or more sensors 118 or 218) about a force and/or torque experienced by the first robotic arm at the moment of initial contact with the anatomical element may be used (together with information about, for example, a velocity of the robotic arm at the moment of the initial contact and a time of the initial contact) to calculate a position of the anatomical element.

The method 300 also comprises comparing the determined position of the anatomical element to an expected position of the anatomical element (step 308). The comparing may be executed by a comparison algorithm such as the comparison algorithm 122. The expected position, as previously described, may be predetermined and/or based on a surgical plan such as the surgical plan 120. The expected position may be based on preoperative imaging of the anatomical element and/or of an anatomical region comprising the anatomical element. The expected position may be a position utilized for preoperative planning (including, for example, navigation and/or robotic guidance), such that a determination that the anatomical element is no longer in the expected position may necessitate updating the preoperative planning (including, for example, the navigation and/or robotic guidance).

In some embodiments, the first robotic arm may be caused to move toward and contact the anatomical element at different times throughout a surgical procedure. Each time, the moment of initial contact between the first robotic arm and the anatomical element may be detected, as described above in connection with the step 304, and the position of the anatomical element at that time may be determined, as described above with respect to the step 306. On the second or any subsequent iteration of the steps 304 and 306, the expected position of the anatomical element may be, for example, the position of the anatomical element as determined during the immediately previous iteration of the steps 304 and 306. By iterating the steps 304 and 306 multiple times during the course of a surgical procedure, any digital models, surgical plans, and/or other information that is based upon or otherwise reflects an expected position of the anatomical element may be updated to reflect a then-current actual position of the anatomical element. Moreover, at any iteration of the steps 304 and 306, an amount or degree of movement of the anatomical element may be determined by comparing the determined position of the anatomical element to the expected position of the anatomical element.

The method 300 further comprises updating a tool trajectory of a second robotic arm, such as the robotic arm 116 or the second robotic arm 217, based on the comparison and/or the compensation parameter when the determined position is offset from the expected position (step 310). Such offset may indicate that the anatomical element has moved from the expected position, and thus, that a predetermined tool trajectory for execution of a surgical procedure may be inaccurate. The tool trajectory may be a trajectory of a tool, such as the tool 228, held by the second robotic arm. As such, the tool trajectory may be updated to accommodate such offset. In embodiments where a compensation parameter is calculated (as described below with respect to step 314), the compensation parameter may be applied to the tool trajectory.

The method 300 also comprises registering the first robotic arm and the second robotic arm to a patient space corresponding to the patient space (step 312). Such registration correlates a pose of the first robotic arm and of the second robotic arm to a patient in a common coordinate system. In some embodiments, the registration may utilize one or more images, including, for example, a virtual model of patient anatomy and/or an image of one or both of the first robotic arm and the second robotic arm. In some embodiments, data generated by one or more sensors other than an optical sensor may be used instead of images. In other embodiments, the method 300 may register the first robotic arm and the second robotic arm to a navigation coordinate system used by a navigation system such as the navigation system 112 or 212.

The method 300 may also comprise calculating a compensation parameter based on the comparing step (step 314). The compensation parameter may be a constant, an algorithm, or any other transformation function that may be applied to a position, path, trajectory, and/or other value generated based on the expected position of the anatomical element to yield a new position, path, trajectory, and/or other value that reflects or is otherwise based on the determined position of the anatomical element. The compensation parameter may be calculated via a compensation parameter algorithm such as the compensation parameter algorithm 124. The compensation parameter maybe based on, for example, a difference between the determined position and the expected position of the anatomical element, or in other words, on the results of the comparison of the determined position to the expected position. In some embodiments, the compensation parameter may further be based on, for example, a position of the first robotic arm and/or the second robotic arm, a force and/or torque sensed by the sensor of the first anatomical arm, a force and/or torque exerted by the second robotic arm sensed by the sensor of the second robotic arm, and/or the like.

The method 300 also comprises securing the first robotic arm to the anatomical element (step 316). In such embodiments, the first robotic arm may be secured to the anatomical element via a mechanical gripper such as the gripper 222. In other embodiments, the first robotic arm may be attached to the anatomical element with one or more screws, clamped to the anatomical element, or otherwise secured to the anatomical element, whether using one or more mechanical fasteners, a chemical adhesive, or otherwise.

The method 300 also comprises detecting movement of the first robotic arm based on data received from the sensor while the first robotic arm is secured to the anatomical element (step 318), and determining a movement of the anatomical element based on the detected movement of the first robotic arm (step 320). Using dimensional information about the first robotic arm (e.g., a length of one or more segments, dimensions of an end effector or other gripper that secures the first robotic arm to the anatomical element, etc.), as well as information from one or more sensors internal to the first robotic arm (including, for example, information about a position of any one portion of the robotic arm relative to a position of any other portion of the robotic arm), a pose of the first robotic arm—and thus of any end effector secured to the first robotic arm—may be determined. Moreover, while the first robotic arm is secured to the anatomical element (whether using a gripper or any other end effector), a pose of the anatomical element may be readily determined based on a known pose of the first robotic arm. Also, any force or torque exerted on the anatomical element that causes movement of the anatomical element will necessarily cause movement of at least a portion of the first robotic arm. As a result, any uncommanded movement (e.g., movement not caused by the first robotic arm's motor(s) or other actuator(s)) of the first robotic arm indicates movement of the anatomical element to which the first robotic arm is secured, and the pose of the first robotic arm (as determined based on information from the one or more internal sensors of the first robotic arm) during and after such movement may be used to determine a pose of the anatomical element during and after such movement. Notably, the connection between the first robotic arm and the anatomical element enables the pose of the anatomical element to be monitored using only the sensors internal to the first robotic arm, and no other sensors.

The method 300 also comprises updating a virtual model of an anatomical portion of the patient—for instance, a virtual model from a surgical plan such as the surgical plan 120 or a virtual model generated pre- or intraoperatively—based on the determined movement of the anatomical element (step 322). In such embodiments, the first robotic arm and/or the second robotic arm may be correlated or otherwise registered to the virtual model, and updating the virtual model may update the registration.

The method 300 also comprises activating the first robotic arm to prevent movement of the anatomical element from the determined position (step 324). In some embodiments, the first robotic arm is used to hold the anatomical element in a desired position and to prevent movement of the anatomical element. In some instances, the first robotic arm may be sufficiently rigid in any given pose to prevent movement of the anatomical element without having to apply a counteractive force and/or torque via the first robotic arm's internal motors or other actuators. In other embodiments, the predicted torques and/or forces from a surgical plan (received, for example, in a step 332, described below) may be used to apply counteractive force(s) and/or torque(s) at one or more time intervals while using the first robotic arm, so that the anatomical element does not move.

The method 300 also comprises causing the second robotic arm to move based on the determined movement of the anatomical element (step 326). In other words, movement of the second robotic arm may be commanded and/or adjusted based on movement of the anatomical element, as detected using the first robotic arm. In some embodiments the first robotic arm may be utilized to detect movement of the anatomical element, but not to reduce or prevent any such movement. In such embodiments, monitoring of a pose of the anatomical element using the first robotic arm enables a trajectory and/or other guidance for controlling the second robotic arm to be adjusted as needed based on the pose of the anatomical element. In other words, the one or more sensors of the first robotic arm provide information about the movement of the first robotic arm (and therefore of the anatomical element) to a computing device such as the computing device 102, and the computing device adjusts a trajectory or other guidance of the second robotic arm based on the movement. To use a simple example, then, if information from the one or more internal sensors of the first robotic arm indicates that the end effector of the first robotic arm has moved one centimeter in a given direction, then the computing device or other controller of the second robotic arm can adjust the trajectory of the second robotic arm by one centimeter in the given direction, thus maintaining a desired relative position or path of the second robotic arm with respect to the anatomical element.

In still other embodiments, the first robotic arm is secured to the anatomical element both to prevent movement of the anatomical element to an extent possible (as described above in connection with the step 324) and to detect movement of the anatomical element when preventative measures are insufficient to prevent movement of the anatomical element so as to enable appropriate adjustment of the movement of the second robotic arm (as described above in connection with the step 326). In such embodiments, the first robotic arm may be sufficiently rigid to prevent at least some movement of the anatomical element, and/or may utilize one or more of its motors or other actuators to apply counteractive force(s) and/or torque(s) to the anatomical element at one or more time intervals (based on, for example, one or more predicted force(s) and/or torque(s) as set forth in a surgical plan) to prevent at least some such movement. However, if and when such rigidity and/or counteractive force(s) and/or torque(s) are insufficient to hold the anatomical element still, and movement of the anatomical element occurs, then the first robotic arm (including the one or more internal sensors thereof) may detect such movement and provide information about the movement to the computing device. The computing device may then adjust a trajectory of the second robotic arm based on the movement to maintain a desired position or path of the second robotic arm relative to the anatomical element.

The method 300 also comprises activating the first robotic arm to move the anatomical element to the expected position (step 328). During a surgical procedure involving the anatomical element, a trajectory or path of the second robotic arm may not be able to be updated to account for movement of the anatomical element, and/or the anatomical element may have moved out of a desired position and/or orientation. At such times, the first robotic arm may be activated to move the anatomical element into, or back into, an expected, desired, or otherwise predetermined position. In some embodiments, movement of the second robotic arm and/or progress in the surgical procedure may be paused while the first robotic arm moves the anatomical element into the predetermined position.

The method 300 also comprises receiving second information from at least one second internal sensor, such as the sensor 118 or 218, of the second robotic arm (step 330). The second information may correspond to at least one of an applied force or an applied torque exerted by the second robotic arm on the anatomical element. More particularly, a tool (e.g., a drill, tap, screwdriver, and/or other tool) held by the second robotic arm may apply a force and/or a torque on the anatomical element during operation thereof. Moreover, the second robotic arm may be configured to press the force against and/or into the anatomical element to increase an effectiveness thereof. In either or both situations, one or more internal sensors of the second robotic arm may detect the force and/or torque applied thereby on the anatomical element, and may provide information corresponding to the detected force and/or torque to a computing device and/or other controller of the first and/or second robotic arm.

In some embodiments, the method 300 may comprise receiving information about an activation of the second robotic arm (which may include, for example, information about activation of a surgical tool held by the second robotic arm). In such embodiments, the computing device or other controller of the first robotic arm may utilize the received information to calculate a predicted force and/or torque that will be experienced by the anatomical element as a result of the activation.

In still other embodiments, the first robotic arm may detected a force and/or torque exerted by the second robotic arm (including, for example, a surgical tool held by the second robotic arm) on the anatomical element, as a result of the force and/or torque being communicated to the first robotic arm via the anatomical element.

The method 300 also comprises causing the first robotic arm to exert at least one of a responsive force or a responsive torque on the anatomical element to counteract the applied force or the applied torque experienced by the anatomical element (step 332). The computing device or other controller of the first robotic arm may calculate, based on the detected or calculated applied force and/or torque, an activation of the one or more internal motors or other actuators of the first robotic arm that is required to counteract the applied force and/or torque. In other embodiments, the computing device or other controller of the first robotic arm may utilize a feedback loop to activate one or more actuators of the first robotic arm in increasing increments for as long as a detected or calculated applied force on the anatomical element is rising, to maintain a given level of activation of the first robotic arm for as long as the detected or calculated applied force is constant, and to decrement the activation of the one or more actuators of the first robotic arm once the detected or calculated applied force begins to decrease. Thus, in such embodiments, the computing device or controller of the first robotic arm does not explicitly calculate a required degree of activation of the first robotic arm, but instead continually adjusts a degree of activation of the first robotic arm in response to the detected or calculated applied force and/or torque.

Figure 4:
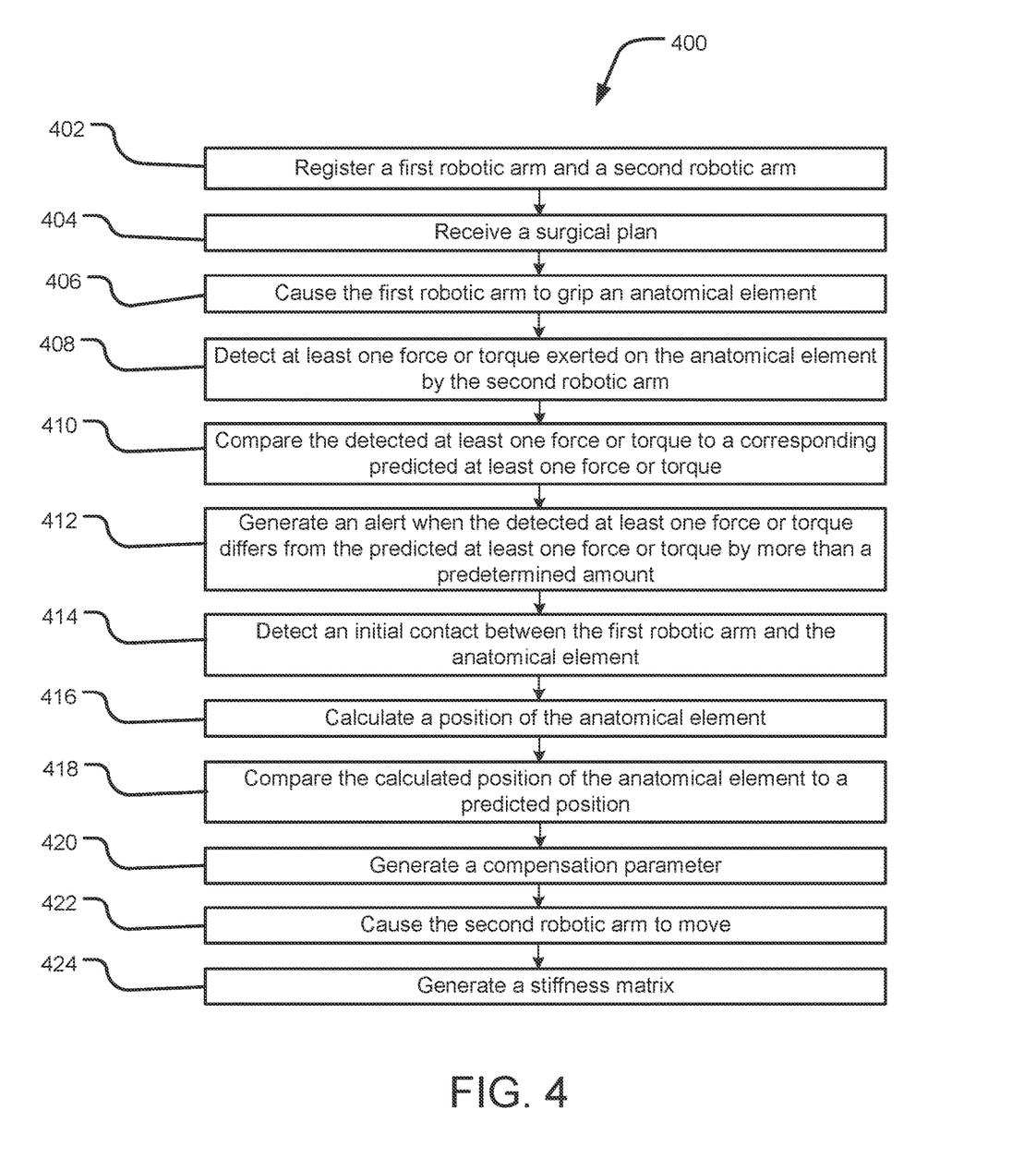
FIG. 4 is a flowchart of a method according to at least one embodiment of the present disclosure.

Turning now to FIG. 4, a method 400 for controlling a robotic arm may be executed in whole or in part, for example, on a computing device such as the computing device 102 or 202 or a similar device, and may utilize one or more other components of the system 100 or 200 or similar components. One or more aspects of the method 400 may be performed by or with a robot such as the robot 114 or 214, a surgeon, or a combination of a surgeon and/or the robot.

The method 400 comprises registering a first robotic arm to a patient space corresponding to a patient (step 402). The first robotic arm may be the robotic arm 116 or the first robotic arm 216, and the second robotic arm may be the robotic arm 116 or the second robotic arm 217. The step 402 may be the same as or similar to the step 312 of the method 300 described above, or vice versa. For example, the registering may correlate a pose of the first robotic arm and of the second robotic arm to a patient in a common coordinate system. In some embodiments, the registration may utilize one or more images, including, for example, a virtual model of patient anatomy and/or an image of one or both of the first robotic arm and the second robotic arm. In some embodiments, data generated by one or more sensors other than an optical sensor may be used instead of images. In other embodiments, the method 400 may register the first robotic arm and the second robotic arm to a navigation coordinate system used by a navigation system such as the navigation system 112 or 212, instead of or in addition to registering the first and second robotic arms to a patient space. In still further embodiments, a coordinate system corresponding to the first robotic arm may be registered to a coordinate system corresponding to the second robotic arm or vice versa, so that both robotic arms are registered to and controllable with respect to a single coordinate space.

The method 400 also comprises receiving a surgical plan (step 404). The surgical plan may be the surgical plan 120. The step 404 may be the same as or similar to the step 302 of the method 300 described above, or vice versa. The surgical plan may be received via a user interface (e.g., the user interface 110) and/or a communication interface (e.g., the communication interface 108) of a computing device such as the computing device 102 or 202, and may be stored in a memory such as the memory 106 of the computing device. The surgical plan includes information about an anatomical element, such as the anatomical element 226, of the patient and/or a surgical task to be completed on the anatomical element. The anatomical element may be a vertebra in some embodiments.

The surgical plan may include information about a position and/or orientation of the anatomical element. The surgical plan may also include information about a second robotic arm, such as the robotic arm 116 or the second robotic arm 217, that may perform the surgical task. The surgical plan may also include information about one or more planned movements of the second robotic arm. In some embodiments, the surgical plan includes a planned trajectory or path of the second robotic arm. The surgical plan may also include an expected position of the anatomical element (e.g., a position and/or orientation of the anatomical element). The surgical plan may further include a predicted force or torque that will be or at least is expected to be exerted on the anatomical element by the second robotic arm (including by a surgical tool held by the second robotic arm), and/or a predicted movement of the anatomical element as a result of interaction between the second robotic arm and the anatomical element.

The method 400 also comprises causing the first robotic arm to grip the anatomical element with a mechanical gripper (step 406). The mechanical gripper may be the gripper 222. The step 406 may be the same as or similar to the step 316 of the method 300 described above, or vice versa. For example, in some embodiments, the first robotic arm may grip the anatomical element at a position provided by the surgical plan. Also, in some embodiments, the first robotic arm may be attached to the anatomical element using one or more screws, clamped to the anatomical element, or otherwise secured to the anatomical element, whether using one or more mechanical fasteners, a chemical adhesive, or otherwise. The gripping or attachment ensures that the anatomical element cannot move relative to the gripper or other end effector and further acts to translate the anatomical element's movement to a movement of the first robotic arm. In other words, movement of the anatomical element moves the first robotic arm via the gripper or other end effector. Further, because the first robotic arm has a known position relative to the anatomical element, a pose of the anatomical element can be determined based on a pose of the first robotic arm.

The method 400 further comprises detecting at least one force or torque exerted on the anatomical element by the second robotic arm (step 408). The detecting may be based on sensor data relating to the at least one force or torque received from at least one internal sensor such as the sensor 118 or 218 of the first robotic arm. In particular, the detecting may be accomplished without the use of any sensor external to the first robotic arm. Because the first robotic arm is secured to the anatomical element, forces sensed by the first robotic arm correlate to forces exerted on the anatomical element by the second robotic arm. The amount of correlation may depend, for example, on the makeup of the anatomical element. Where the anatomical element is a bone or other hard tissue, the amount of correlation may be high, because a force exerted on one point of the anatomical element will largely be translated to another point of the anatomical element. Where the anatomical element comprises soft tissue (or tissue that is not as hard as a bone), the amount of correlation may be low, because the anatomical element may absorb some of the force by deforming or otherwise.

Detecting the at least one force or torque may include receiving sensor data correlating to the at least one force or torque from the at least one internal sensor. The sensor data may be received by a computing device such as the computing device 102 or 202, or by another controller of the first and/or second robotic arm. In some embodiments, the sensor data may be received via the user interface and/or via the communication interface of the computing device, and may be stored in the memory. In some embodiments, the sensor data may be indirectly received via any other component of the system or a node of a network to which the system is connected. The sensor data may include force data, torque data, and/or positional data (e.g., data corresponding to a relative position of one or more segments of the robotic arm with respect to one or more other segments of the robotic arm) of the first robotic arm and/or the second robotic arm.

The method 400 also comprises comparing the detected force or torque to a corresponding predicted force or torque described in the surgical plan (step 410). The comparing may be executed by a comparison algorithm such as the comparison algorithm 122. The predicted force or torque may be based on, for example, information about a hardness of the anatomical element, information about a surgical task to be carried out on the anatomical element, information about a tool that will be used to carry out the surgical task (including, for example, information about a force and/or torque produced by the tool), information about an amount of force or torque that the anatomical element can receive without causing the anatomical element to move out of position, and/or other information. For example, where the surgical task is to drill a hole in a vertebra in preparation for implantation of a pedicle screw therein, the predicted force or torque may be based on information about a torque produced by the drill that will be used to drill the hole and information about the down-force that will be applied by the second robotic arm during the drilling process. In some embodiments, the amount of force and/or torque expected to be applied may be selected and/or adjusted based on information about an amount of force or torque that the anatomical element can receive without causing the anatomical element to move out of position, although in other embodiments (e.g., where the first robotic arm will be used to hold the anatomical element in position), this consideration may not be relevant. By comparing the predicted force or torque with the detected force or torque, movement of the anatomical element can be predicted and/or determined simply based on a mismatch between the detected force or torque and the predicted force or torque.

The method 400 also include generating an alert when the detected force or torque differs from the predicted force or torque by more than a predetermined amount (step 412). Such alert may be audible, visual, haptic, or any combination thereof, and may be displayed or otherwise generated or emitted from, for example, a user interface such as the user interface 110, the computing device, and/or the robot.

In some embodiments, the method 400 also comprises detecting an initial contact between the first robotic arm and the anatomical element based on information from the at least one sensor (step 414), and calculating a position of the anatomical element at a time of the detected initial contact (step 416). The steps 414 and 416 may be the same as or similar to the steps 304 and 306 of the method 300 described above, or vice versa. The position of the anatomical element may be determined, for example, based on the information or sensor data from one or more internal sensors of the first robotic arm. Such information or sensor data may comprise, for example, position information of the first robotic arm (e.g., as detected at the time of the initial contact), force and/or torque data regarding a force and/or torque experienced by the first robotic arm during the initial contact, and/or other information useful for determining a position of the first robotic arm and, based on that determined position, a position of the anatomical element. Because the first robotic arm contacts the anatomical element, the positional data of the first robotic arm may correlate to the position of the anatomical element. With respect to method 400, where the first robotic arm is subsequently secured to the anatomical element, the position of the anatomical element, once determined, may be correlated to a position of the first robotic arm. For example, a position of the first robotic arm may be determined from the at least one sensor, and a relative position of the anatomical element and the first robotic arm may be determined using, for example, information about the dimensions of the first robotic arm, dimensions of the anatomical element, and/or information from the navigation system.

The method 400 also comprises comparing the calculated position of the anatomical element to a predicted position of the anatomical element from the surgical plan (step 418). The step 418 is the same as or similar to the step 308 of the method 300 described above, or vice versa. For example, the comparing may be executed by a comparison algorithm such as the comparison algorithm 122. The expected position, as previously described, may be predetermined and/or based on the surgical plan. The expected position may be based on preoperative imaging of the anatomical element and/or of an anatomical region comprising the anatomical element. The expected position may be a position utilized for preoperative planning (including, for example, navigation and/or robotic guidance), such that a determination that the anatomical element is no longer in the expected position may necessitate updating the preoperative planning (including, for example, the navigation and/or robotic guidance).

The method 400 also comprises generating a compensation parameter based on the comparison step (step 420). The step 420 may be the same as or similar to the step 314 of the method 300 described above, or vice versa. The compensation parameter may be a constant, an algorithm, or any other transformation function that may be applied to a position, path, trajectory, and/or other value generated based on the expected position of the anatomical element to yield a new position, path, trajectory, and/or other value that reflects the determined position of the anatomical element. The compensation parameter may be calculated via a compensation parameter algorithm such as the compensation parameter algorithm 124. The compensation parameter may be based on, for example, a difference between the determined position and the expected position of the anatomical element, or in other words, on the results of the comparison of the determined position to the expected position. In some embodiments, the compensation parameter may further be based on, for example, a position of the first robotic arm and/or the second robotic arm, a force sensed by the sensor of the first anatomical arm, a force exerted by the second robotic arm sensed by the sensor of the second robotic arm, and/or the like.

The method 400 also comprises causing the second robotic arm to move at least in part based on the compensation parameter (step 422). In some embodiments, the compensation parameter may shift a trajectory of the second robotic arm to accommodate a determined position of the anatomical element. For example, if the anatomical element shifts one centimeter in a direction, then the trajectory of the second robotic arm may be shifted one centimeter the same direction. In other embodiments, the compensation parameter may be utilized to calculate a responsive force or responsive torque applied by the first robotic arm, a needed movement of the anatomical element by the first robotic arm, and/or a required activation of the first robotic arm to prevent movement of the anatomical element.

The method 400 also comprises generating a stiffness matrix (step 424). The stiffness matrix is generated once the first robotic arm is secured to the anatomical element, by causing the first robotic arm to move in each of six degrees of freedom. The movements may be small motions. Information about the force applied by the first robotic arm (and/or any component thereof) to cause the movement, as well as information about the amplitude of the movement, may be used to generate stiffness data for the anatomical element in each degree of freedom, thus resulting in a stiffness matrix. Predicted motion of the anatomical element may be determined based on the stiffness matrix and known forces and/or moments generated by the second robotic arm. The predicted motion may be compared to a motion of the anatomical element detected using the first robotic arm. When the detected motion is different from the predicted motion, then the difference may indicate that an undesired motion of the anatomical element occurred. For example, when the second robotic arm drills (e.g., using a surgical drill held by the second robotic arm) into an anatomical element, (e.g., a bone) held by the first robotic arm then the expected or predicted applied force is along the drilling direction and the expected or predicted torque is around the drill's longitudinal axis. Using the stiffness matrix, and the predicted applied force and the predicted torque, a predicted motion of the bone can be calculated. When, a different motion is detected by the first robotic arm (e.g., when the predicted motion does not match the detected motion), that difference may reflect a skiving. In some embodiments, detecting the forces and torques using the first robotic arm (as opposed to detecting the motion of the anatomical element) and comparing the detected forces and torques to the expected or predicted forces and torques also provides the necessary information of possible skiving. The same can be achieved in another embodiment involving minimally invasive surgical procedures where the first robotic arm does not directly hold the anatomical element, but instead holds a device connecting rigidly to the anatomical element. The device may be K-wire or a dynamic reference frame.

Methods and systems for tracking anatomical motion and/or controlling a robotic arm according to at least some embodiments of the present disclosure beneficially provide notification of or compensation for undesired movement of an anatomical element during a surgical procedure. Such notification may allow for a surgeon or operator to pause the procedure, thus preventing further damage to patient anatomy. Such compensation provides for self-correcting tool movement, and thus may also prevent unnecessary damage to patient anatomy. Further, the use of internal, integrated sensors beneficially provide for accurate sensing of anatomical movement within a single coordinate space.

As may be appreciated based on the foregoing disclosure, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the method 300 and 400). One or more steps of the methods described herein may be performed in an order other than the order in which they are described herein.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of tracking anatomical motion, comprising:
   detecting, by a processor, based on information received from at least one internal sensor of a first robotic arm, an initial contact between the first robotic arm and an anatomical element of a patient, wherein the first robotic arm rigidly holds the anatomical element of the patient in place;
   determining, by the processor, based on the information, a position of the anatomical element;
   comparing, by the processor, the determined position of the anatomical element to an expected position of the anatomical element; and
   when the determined position is offset from the expected position, updating, by the processor, a tool trajectory of a second robotic arm based on the comparison.

2. The method of claim 1, further comprising:
   registering, by the processor, the first robotic arm and the second robotic arm to a patient space corresponding to the patient.

3. The method of claim 1, wherein the expected position is based on a surgical plan.

4. The method of claim 1, further comprising:
   calculating, by the processor, a compensation parameter based on the comparison;
   wherein updating the tool trajectory of the second robotic arm based on the comparison comprises applying the compensation parameter to the tool trajectory.

5. The method of claim 1, wherein the at least one internal sensor comprises a force sensor and a torque sensor.

6. The method of claim 1, wherein the at least one internal sensor comprises an encoder.

7. The method of claim 1, further comprising:
   causing, by the processor, the first robotic arm to be secured to the anatomical element; and
   activating, by the processor, the first robotic arm to move the anatomical element to the expected position.

8. The method of claim 1, further comprising:
   causing, by the processor, the first robotic arm to be secured to the anatomical element;
   detecting, by the processor, based on data received from the at least one internal sensor, movement of the first robotic arm; and
   determining, by the processor, based on the detected movement, a movement of the anatomical element.

9. The method of claim 8, further comprising:
   updating, by the processor, a virtual model of an anatomical portion of the patient based on the determined movement of the anatomical element.

10. The method of claim 8, further comprising:
    causing, by the processor, the second robotic arm to move based on the determined movement of the anatomical element.

11. The method of claim 1, further comprising:
    causing, by the processor, the first robotic arm to be secured to the anatomical element; and
    activating, by the processor, the first robotic arm to prevent movement of the anatomical element from the determined position.

12. The method of claim 11, wherein the information is first information, the method further comprising:
    receiving, by the processor, second information from at least one second internal sensor of the second robotic arm, the second information corresponding to at least one of an applied force or an applied torque exerted by the second robotic arm on the anatomical element; and
    causing, by the processor, the first robotic arm to exert at least one of a responsive force or a responsive torque on the anatomical element to counteract the applied force or the applied torque.

13. A method of controlling a robotic arm, comprising:
    registering, by a processor, a first robotic arm and a second robotic arm to a patient space corresponding to a patient;
    receiving, by the processor, a surgical plan comprising information about an anatomical element of the patient and a surgical task to be completed on the anatomical element by the second robotic arm;
    causing, by the processor, the first robotic arm to grip the anatomical element with a mechanical gripper and rigidly hold the anatomical element; and
    detecting, by the processor, based on sensor data received from at least one internal sensor of the first robotic arm and without use of data from any external sensor, at least one force or torque exerted on the anatomical element by the second robotic arm.

14. The method of claim 13, further comprising:
comparing, by the processor, the detected at least one force or torque to a corresponding predicted at least one force or torque described in the surgical plan; and
generating, by the processor, an alert when the detected at least one force or torque differs from the corresponding predicted at least one force or torque by more than a predetermined amount.

15. The method of claim 13, further comprising:
detecting, by the processor, an initial contact between the first robotic arm and the anatomical element, based on information from the at least one internal sensor;
calculating, by the processor, a position of the anatomical element based on a position of the first robotic arm at a time of the detected initial contact; and
comparing, by the processor, the calculated position of the anatomical element to a predicted position of the anatomical element from the surgical plan.

16. The method of claim 15, further comprising:
generating, by the processor, a compensation parameter based on the comparison; and
causing, by the processor, the second robotic arm to move based at least in part on the compensation parameter.

17. The method of claim 15, wherein the anatomical element is a vertebra.

18. A system for accounting for anatomical movement during a surgical procedure, comprising:
a working robotic arm;
a detecting robotic arm comprising at least one internal sensor configured to detect at least one of a force or a torque exerted on the working robotic arm;
at least one processor; and
at least one memory storing instructions for execution by the at least one processor that, when executed, cause the at least one processor to:
receive a surgical plan comprising information about an anatomical element of a patient and a surgical task to be completed on the anatomical element by the working robotic arm;
correlate a position of the detecting robotic arm to a position of the anatomical element;
detect, based solely on sensor data received from the at least one internal sensor, a movement of the detecting robotic arm resulting from a movement of the anatomical element during execution of the surgical task, wherein the robotic arm rigidly holds the anatomical element; and
control movement of the detecting robotic arm during execution of the surgical task based on the detected movement.

19. The system of claim 18, wherein the at least one internal sensor comprises an encoder configured to sense at least one of an applied force or an applied torque.

20. The system of claim 18, wherein the surgical plan comprises information about a predicted force or torque to be exerted on the anatomical element by the working robotic arm during execution of the surgical task, and the at least one memory stores additional instructions for execution by the at least one processor that, when executed, cause the at least one processor to:
detect, based solely on information received from the at least one internal sensor, a force or a torque exerted on the anatomical element by the working robotic arm; and
compare the detected force or torque to the predicted force or torque.

* * * * *